United States Patent
Ezzedine

(10) Patent No.: US 7,608,076 B2
(45) Date of Patent: *Oct. 27, 2009

(54) MINIMALLY INVASIVE COLLAPSIBLE SURGICAL REAMER

(75) Inventor: Mahmoud Ezzedine, Bienne (CH)

(73) Assignee: Greatbatch Medical S.A., Orvin (CH)

( * ) Notice: Subject to any disclaimer, the term of this patent is extended or adjusted under 35 U.S.C. 154(b) by 385 days.

This patent is subject to a terminal disclaimer.

(21) Appl. No.: 11/380,006

(22) Filed: Apr. 25, 2006

(65) Prior Publication Data

US 2006/0264958 A1 Nov. 23, 2006

Related U.S. Application Data

(60) Provisional application No. 60/675,925, filed on Apr. 29, 2005.

(51) Int. Cl.
*A61B 17/00* (2006.01)

(52) U.S. Cl. .............................. 606/81; 606/80; 606/79

(58) Field of Classification Search .................. 606/80, 606/81, 79, 86 R, 82, 83, 84, 85; 623/22.21, 623/22.22, 22.23, 22.24, 22.25, 22.26, 22.27, 623/22.28, 22.29
See application file for complete search history.

(56) References Cited

U.S. PATENT DOCUMENTS

| | | | |
|---|---|---|---|
| 3,702,611 A | 11/1972 | Fishbein | |
| 5,658,290 A | 8/1997 | Lechot | |
| 6,106,536 A | 8/2000 | Lechot | |
| 6,168,600 B1 * | 1/2001 | Grace et al. | 606/81 |
| 6,264,647 B1 | 7/2001 | Lechot | |
| 6,918,914 B2 * | 7/2005 | Bauer | 606/81 |
| 7,097,646 B2 * | 8/2006 | Schantz | 606/81 |
| 2004/0167528 A1 * | 8/2004 | Schantz | 606/81 |
| 2006/0025774 A1 * | 2/2006 | Fishbein et al. | 606/81 |
| 2006/0217730 A1 * | 9/2006 | Termanini | 606/81 |

FOREIGN PATENT DOCUMENTS

| | | | | |
|---|---|---|---|---|
| WO | PCT/US99/05951 | 9/1999 | | |
| WO | PCT/US02/21310 | 8/2002 | | |
| WO | WO 03/092513 | * 11/2003 | | 606/81 |

* cited by examiner

*Primary Examiner*—Eduardo C Robert
*Assistant Examiner*—Jan Christopher Merene
(74) *Attorney, Agent, or Firm*—Michael F. Scalise

(57) ABSTRACT

A surgical reamer (10) for cutting a bone socket is provided, defining a drive axis, an apex. The reamer (10) further includes (a) a fixed support portion (12) aligned with the drive axis and having at least one radial cutting blade (16c); (b) a pivoting portion (20) aligned with the drive axis and pivotable about this axis, the pivoting portion supporting at least one radial cutting blade (20c); and (c) a pivoting joint (22) wherein the pivoting portion may be pivoted toward and away from the fixed portion (12) so as to expand or contract the reamer in relative overall size and wherein the reamer has a cutting orientation in which the cutting blades (16c, 20c) are supported against relative rotational movement when cutting bone. A surgical kit and method employing the inventive reamer are also disclosed.

22 Claims, 6 Drawing Sheets

MINIMALLY INVASIVE COLLAPSIBLE SURGICAL REAMER

CROSS REFERENCE TO RELATED APPLICATIONS

This application claims priority to U.S. Provisional Application Ser. No. 60/675,925 of the same title, filed Apr. 29, 2005, the content of which is incorporated by reference hereto and relied upon.

TECHNICAL FIELD

This invention generally relates to surgical reamers, particularly those used for cutting a domed-shaped cavity in a bone, more particularly in an acetabulum, to prepare the bone surface for receiving an implantable prosthesis.

BACKGROUND OF THE INVENTION

An objective of orthopedic surgery is to continue developing improved devices and methods that are less invasive to the patient. These efforts include minimizing the size of the incision required in order to effectively employ surgical instrumentation in the preparation of a bone cavity or socket to receive an implant in, e.g., an acetabular reaming procedure. A way to minimize the incision is to optimize the profile that the reamer presents to the incision when inserted therethrough, which is referred to herein as minimizing its "static insertion profile area". By simplifying the surgical steps required, the reamer design can further lessen total inter-operative time and hence decrease the risks generally associated with longer surgical procedures.

Hollow domed acetabular reamers with hemispherical shapes have previously been disclosed, e.g., PCT/US99/05951 and U.S. Pat. Nos. 5,658,290 and 6,264,647, the content of which are incorporated by reference thereto, which are assembled to driving shafts for controlled rotation about a cut axis during the reaming operation. Such prior art acetabular reamers present a circular static insertion profile area having no cords (i.e., no straight sides) when entering the surgical incision, generating a circular dynamic profile area upon rotation of the reamer in the bone socket. A cotyloid reamer is shown in U.S. Pat. No. 6,106,536 (the contents of which is incorporated by reference thereto) having a much different i.e., lop-sided construction compared to the prior acetabular reamers. This cotyloid reamer presents a semi-circular static insertion profile area (i.e., having one cord/straight side) to the surgical incision, which is lesser in profile size than the circular dynamic profile area generated upon rotation of the reamer such as against the bone.

Another objective of orthopedic surgery is to develop instrumentation that is more handily and efficiently used while accurately maintaining a precise cut of the bone socket, in order to minimize inter-operative time. The above-mentioned patent documents also discuss various alternative connections by which their reamers may be functionally assembled to a handle, such assemblies including alignment structures on the reamer and handle allowing controlled rotation of the reamer in the bone socket to further a precision cut.

PCT US02/21310 discloses a reamer that seeks to reduce the static insertion profile area of the reamer to minimize the size of the surgical incision, while providing a precise cut of the desired bone cavity. This reamer employs connections between the reamer and shaft that are designed to perform with a less invasive reamer insertion profile. These connections function with different handles having a variety of bayonet or other assembly connections, and are independent of reamer geometry. This reamer further provides a tool-shaft connection to either a conventional or a less invasive geometry, which allows bone and other organic matter trapped in the reamer, to be removed effectively. The entire contents of the aforesaid PCT/US02/21310 are expressly incorporated by reference herein and relied-upon.

The above-mentioned patent documents have respectively discussed reamers with static insertion geometries that generate dynamic cutting profiles by rotation of the reamer. Generally, there is otherwise no radial expansion or collapsing of the static structure itself.

U.S. Pat. No. 3,702,611, the content of which are incorporated by reference thereto, discloses a reamer having radially expandable blades that are actuated by cam elements to expand the cutters progressively in response to axial thrust exerted on the drive shaft by the surgeon with the reamer head seated in the acetabulum. A spring is used to contact the cutters when the remaining operation is stopped. The inventor's purpose was to provide radially expandable blades to accurately bottom-out the reamer by using the axial movement (by the surgeon) and radial expansion (of the blades) in combination with one another. However, the cutting structure described by the '611 patent contemplates the use of bladed cutting members rather than a domed apex and/or cutting panels each presenting multiple discrete cutting sites, (e.g., of the "cheese grater" type employed by other approaches already discussed above.

Accordingly, it would be desirable to have a reamer (more particularly an acetabular reamer) that is collapsible during passage through a surgical incision then expandable for reaming the bone socket and for collection of debris.

It would be further desirable to provide a hollow dome-shaped reamer having the immediately aforementioned objects, in order to improve accuracy of cut when bottoming-out the reamer in a bone socket, as well as improve the collection of debris.

SUMMARY OF THE INVENTION

A surgical reamer for cutting a bone socket is provided, defining a drive axis and an apex. The reamer further includes (a) a fixed support portion aligned with the drive axis and having at least one radial cutting blade; (b) a pivoting portion aligned with the drive axis and pivotable about this axis, the pivoting portion supporting at least one radial cutting blade; and (c) a pivoting joint wherein the pivoting portion may be pivoted toward and away from the fixed portion so as to expand or contract the reamer in relative overall size and wherein the reamer has a cutting orientation in which the cutting blades are supported against relative rotational movement when cutting bone. A surgical kit and method employing the inventive reamer are also disclosed.

According to a second aspect of the present invention, there is provided a surgical kit for cutting a bone socket.

According to a third aspect of the present invention, there is provided a surgical method for cutting a bone socket in a patient.

Each of the above-listed aspects and preferred embodiments of the present invention is most preferably an acetabular reamer. It is further preferred that the reamer has a locking mechanism that alternately maintains the cutting members in a radially collapsed insertion profile and in a larger, radially expanded cutting profile, as assumed in the description elucidated above.

An advantage of the present invention is a reamer that necessitates a smaller sized surgical incision, compared with conventional reamers, as well as providing a minimally invasive tool contour that eases its surgical introduction through the incision into the bone cavity for reaming, all of the above while providing a precise shaping of the desired bone cavity.

Another advantage of a preferred reamer of the present invention is ease of extraction from the bone cavity through a relatively smaller surgical incision, via a minimally invasive tool profile.

Another advantage of a preferred reamer of the present invention is its ready access for removal of debris for collection.

Other objects and advantages will become apparent to those skilled in the art, upon reviewing the Figures of the Drawings, in conjunction with the Detailed Description set forth further below, wherein references to numerals corresponds to like references in the Drawings.

DETAILED DESCRIPTION OF THE PREFERRED EMBODIMENT(S)

Figure 1:
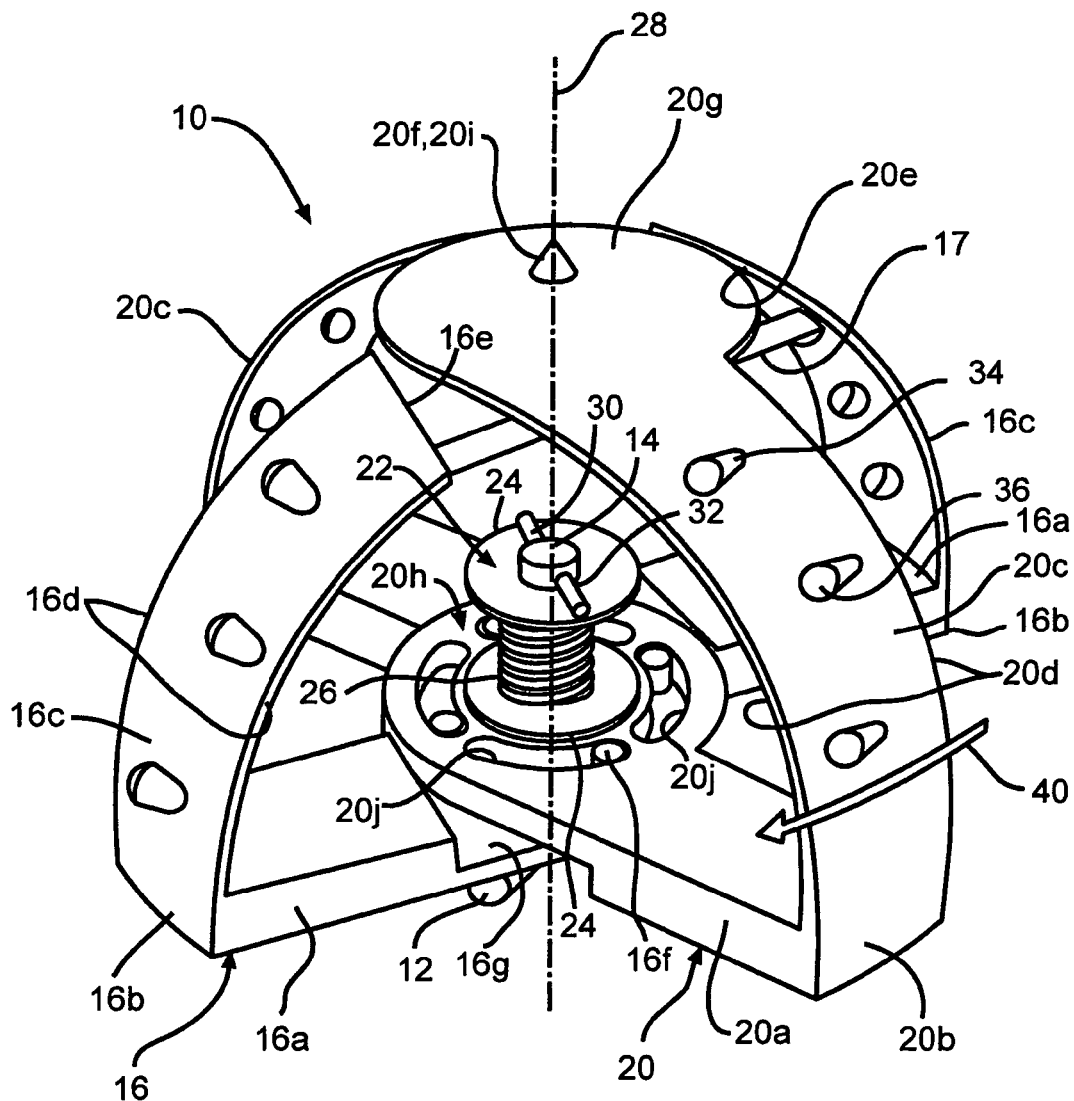
FIG. 1 is a perspective view of the reamer of the invention in an expanded state.
Figure 2:
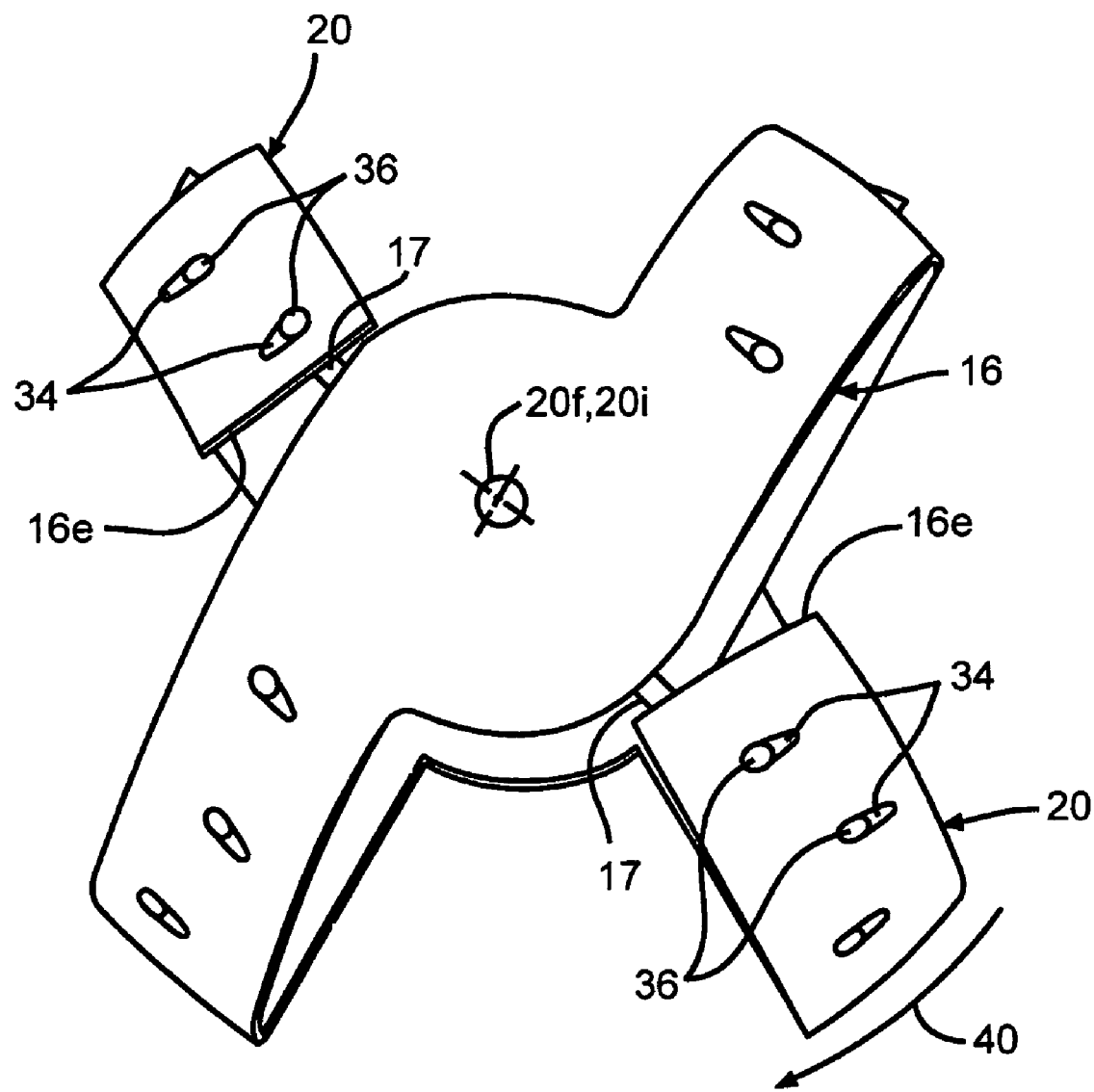
FIG. 2 is a top view of the reamer of the invention in an expanded state.
Figure 3:
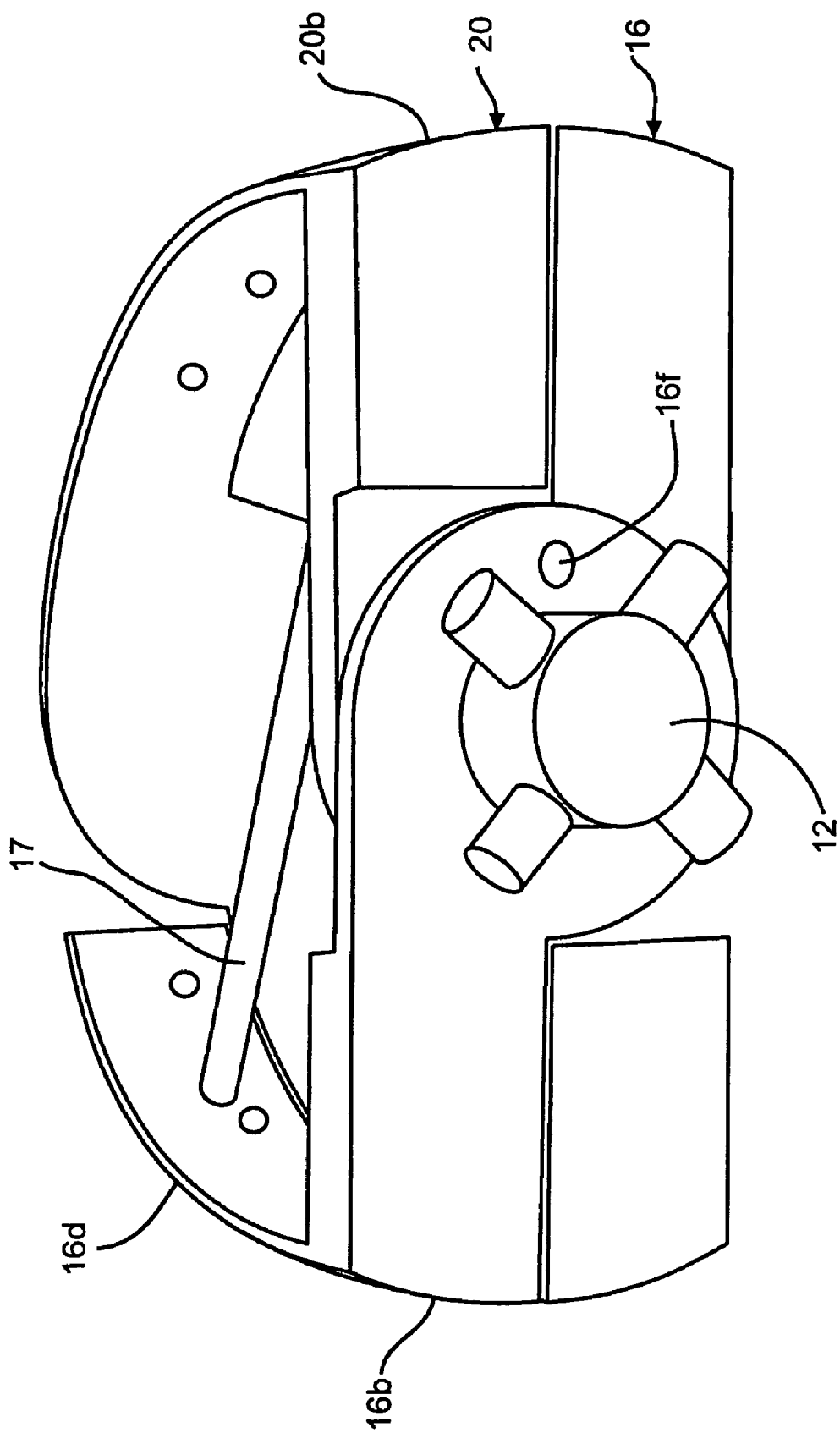
FIG. 3 is a bottom, perspective view of the reamer of the invention, in a fully retracted state.

Referring to FIGS. 1-3, a surgical reamer for cutting a bone socket, preferably an acetabular reamer is generally shown at 10 according to one aspect of the present invention. The reamer 10 is preferably hemispherical in shape, resembling a dome, and is made up of a drive interface 12, a fixed support portion 16, a pin 14, a pivoting portion 20 and a pivoting joint 22. The drive interface 12 is attached to the fixed support portion 16 and is aligned with the drive axis 28. The drive interface 12 interfaces with a driver or tool holder 54 (see FIG. 4) such as that disclosed in U.S. Pat. No. 6,264,647 issued Jul. 24, 2001, the contents of which are incorporated herein by reference thereto. The fixed portion 16 has two opposed radial cutting blades 16c mounted to latitudinal end surfaces 16b of fixed radial arms 16a. The cutting blades 16c extend upwardly from the distal end of the radial arm 16a, toward an end surface 16e, approximately aligned with a polar latitude of the hemispherical form of the reamer. A connector bar 17 extends between opposed blades 16c, proximate the ends surfaces 16e, closing the structure and supporting the cutting blades. The pin 14 is fixed to the fixed portion 16 and extends axially from a surface 16g of the fixed portion.

The pivoting portion 20 is aligned with the drive axis 28 and is pivotable about this axis, having two opposed radial cutting blades 20c connected together by a thin, hemispherically formed structure that extends from a latitudinal surfaces 20b to a polar surface 20g, thereby closing the pivoting portion and interlocking the pivoting portion with that of the fixed portion 16 such that they are linked together in a matched assembly.

The pivoting joint 22 is made up of the pin 14 and washers 24, as well as a compression spring 26 mounted in compression between the washers on the pin, one washer being restrained against a surface 20h of the pivoting portion 20 and the other being restrained against a cotter pin 30, mounted in a cross hole 32 in the pin 14. The spring 26 applies pressure so as to maintain the fixed portion 16 and pivoting portion 20 in operational relationship, namely, in a proper cutting relationship, one set of cutting blades 16c with respect to the other set 20c, so as to maintain the cutting blades on the imaginary surfaces of a single hemispherical cutting from presenting a circular insertion profile when inserted through an incision. Further, the pivot joint 22 enables the pivoting portion 20 and the fixed portion 16 to be pivoted toward and away from each other so as to expand or contract the reamer 10 in relative overall size. The reamer 10 has a cutting orientation in which the cutting blades 16c, 20c are supported against relative rotational movement when cutting bone, and, in this position, are disposed approximately at least 90 degrees one from the other.

A blocking mechanism is made up of a series of pins 16f radially spaced apart about the axis 28 and extending parallel to the axis 28 and perpendicular to a surface 16g of the fixed portion 12, in a direction from the surface 16g toward the apex 20f. The pins 16f pass through corresponding circumferential slots 20j, which permit limited relative rotation of the pivoting portion 20 about the pin 14 but which stop and block the cutting blades 16c, 20c in a preferred cutting position, preventing further relative rotation and fixing the assembly in a cutting position (as shown in FIGS. 1 and 2) when cutting bone. In a first, closed position as shown in FIG. 3, the reamer 10 is in a position in which the pivoting portion 20 and the fixed support portion 16 are collapsed into a relatively small overall size, thus facilitating insertion through an incision. In a second, expanded position (again, as shown in FIGS. 1 and 2), the reamer 10 is in an optimal position for cutting bone. The reamer 10 is automatically brought into this position by cutting forces; rotation of the reamer 10 against tissue creates friction therebetween which acts to open the reamer into an expanded cutting position in which the pivoting portion 20 and fixed support portion 16 are most widely spaced apart from one another.

Preferably, the cutting blades 16c, 20c are longitudinal sections of a dome, more preferably formed with discrete open cutting sites having raised teeth 34 adjacent openings 36 for allowing for passage of debris while reaming the bone socket. The polar surface 20g is further provided with a centering spike 20i (or pilot drill) to aid in positioning the reamer 10 within the bone socket for more controlled reaming.

Figure 4:
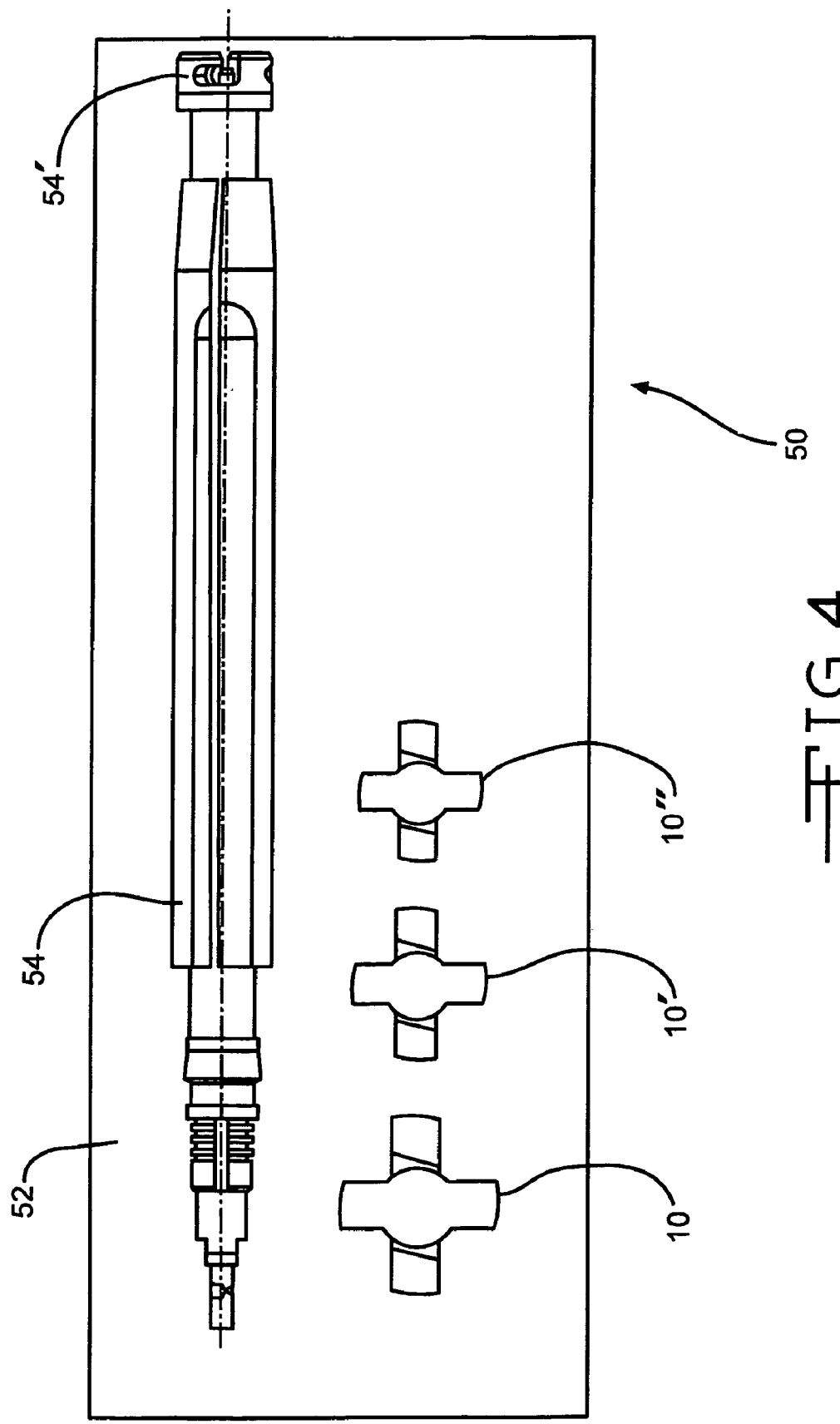
FIG. 4 is a top view of a kit of the invention.

Referring now to FIG. 4, according to a second aspect of the present invention, there is provided a surgical kit 50 for cutting a bone socket. The kit 50 includes a case 52 in which a plurality of reamers 10, 10', 10" of the type described above, as well as a drive tool 54 may be conveniently organized. The reamers 10, 10', 10" come in an array of sizes corresponding to the needs of individual patients. The drive tool 54 includes a quick-disconnect coupling for engaging and disengaging the reamer with a source of rotary power. Another suitable instrument holder is described in U.S. Pat. No. 5,658,290, the entire contents of which are incorporated by reference herein and relied-upon.

Figure 5:
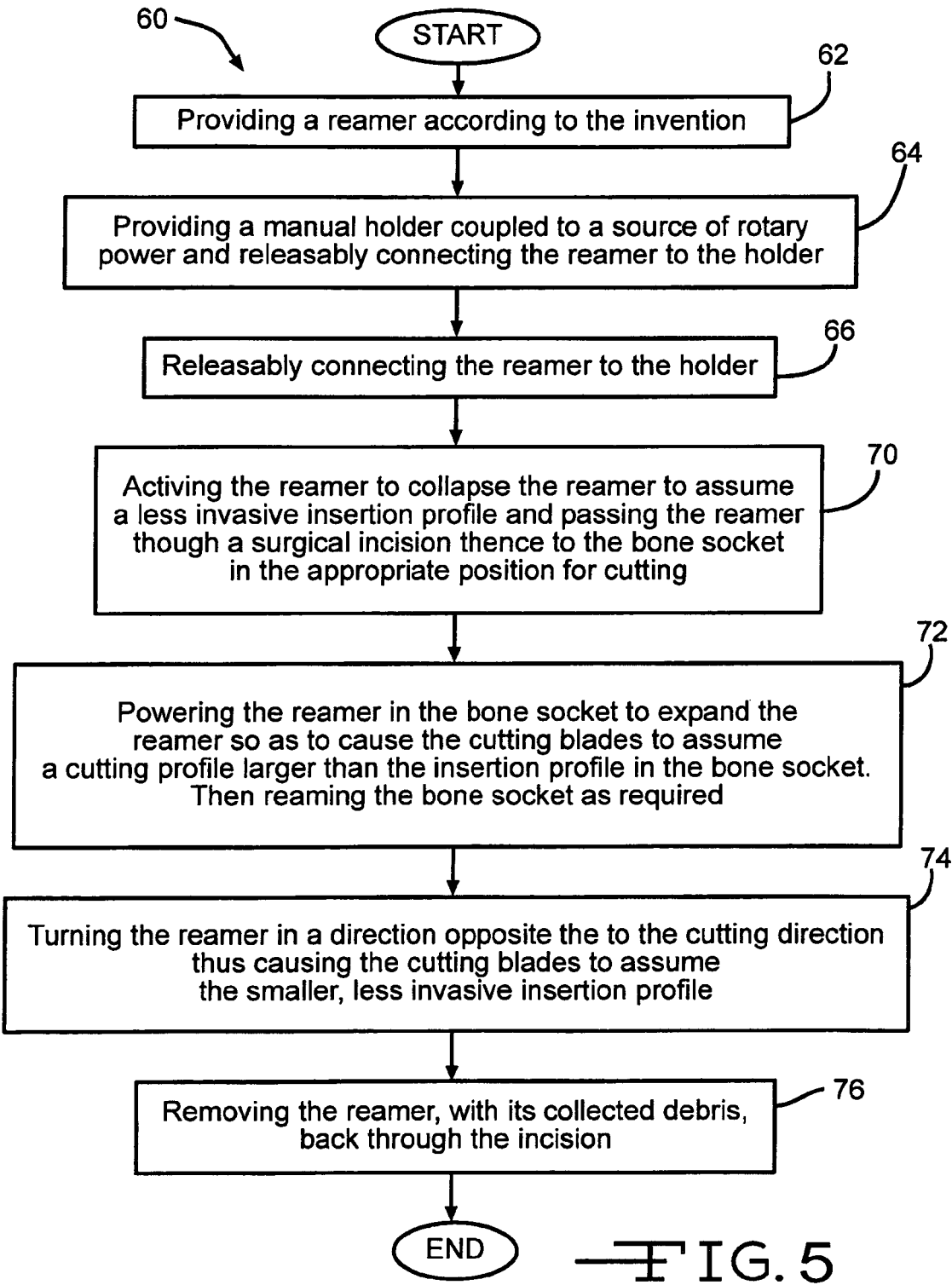
FIG. 5 is a flow chart of the method of the invention.

Referring now to FIG. 5, according to a third aspect of the present invention, there is provided a surgical method 60 for cutting a bone socket in a patient. The method 60 includes the following steps. In a first step 62, a reamer 10 is provided as described above. In a second step 64, a tool driver 54 is provided, coupled to a source of rotary power. In a third step 66, the reamer 10 is releasably connected to the holder. In a fourth step 70, the reamer 10 is activated to collapse the reamer to assume a less invasive insertion profile and passing the reamer through a surgical incision thence to the bone socket in the appropriate position for cutting. In a fifth step 72, the reamer 10 is powered in the bone socket to expand the reamer so as to cause the cutting blades 16c, 20c, to assume a cutting profile larger than the insertion profile in the bone socket, then reaming the bone socket as required. In a sixth step 74, the reamer 10 is turned in a direction opposite to the cutting direction 40, thus causing the cutting blades 16c, 20c to assume the smaller, less invasive insertion profile. In a seventh step 76, the reamer 10 is hence removed, with its collected debris, back through the incision.

Each of the above-listed aspects and preferred embodiments of the present invention is most preferably an acetabular reamer 10. It is further preferred that reamer 10 has a remotely actuated locking mechanism (not shown) that may be selectively actuated to alternately maintain cutting blades 16c and 20c in a radially collapsed insertion profile or in a radially expanded cutting position as assumed in the description elucidated above. The locking mechanism could include, for example, an actuation shaft that extends within a hollow axial passageway in the holder 54 and which would actuate a pin fixed to slide in a corresponding hole of the fixed support portion 16, selectively from a position slidably fixed to the fixed support portion in and out of holes in the pivoting portion 20, such holes receiving the end of the pin and being positioned for the purposes of locking the pivoting portion in an open cutting, and closed, low profile, insertion position. Further, a dual function torsion and compression spring (not shown) may be used to both hold the fixed support portion 12 and pivoting portion 20 together and bias the assembly in either a normally expanded or a normally retracted position, as the particular surgical need may suggest. In addition, the radial blades need not have a locking mechanism at all, but rather open upon use, held open by the normal cutting forces involved while rotating clockwise against the structure to be cut, and close when the blades are urged counterclockwise.

Figure 6:
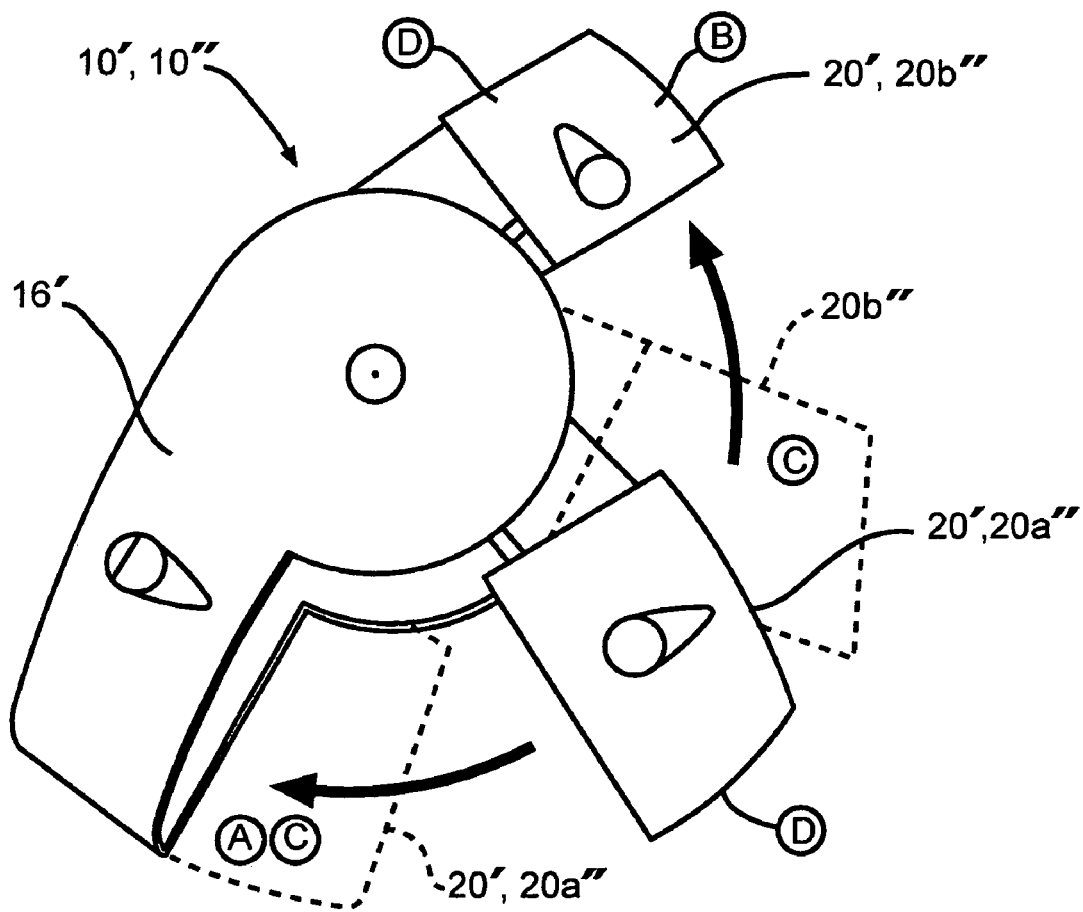
FIG. 6 is a top view of an alternate embodiment of the invention.

Now referring to FIG. 6, in a first alternate embodiment, a reamer 10' includes two cutting blades 16c' and 20c', which present a small insertion profile when blade 20' is positioned adjacent to blade 16c' such as in position A. The blade 20' may then be opened such that it is opposite blade 16c', in position B. In a second alternate embodiment, a reamer 10" includes three cutting blades 16c', 20a", and 20b". In such an embodiment, the rotating blades 20a" and 20b" which are connected together in one rotating unit, present a small profile for entry through an incision in position C, and more toward a cutting position in which they are more evenly spaced about the circumference in position D (note that the spacing of the blades shown is not in the final position, but in an intermediate position, the final position being approximately spaced 120 degrees from one another).

In an advantage of the present invention, the reamer 10 necessitates a smaller sized surgical incision, compared with conventional reamers, as well as provides a minimally invasive tool contour that eases its surgical introduction through the incision into the bone cavity for reaming, all of the above while providing a precise shaping of the desired bone cavity.

In another advantage, the reamer 10 provides a means of ease of extraction from the bone cavity through a relatively smaller surgical incision, via a minimally invasive tool profile.

In another advantage, the reamer 10 is the ready access of its interior for collection of bone debris for grafting.

While one or more preferred embodiments of the present invention have been described, it should be understood that various changes, adaptations and modifications might be made without departing from the spirit of the invention and the scope of the appended Claims. For example, the reamer may depart from the generally hemispherical shape, being of a conical shape or even a truncated conical shape without departing from the spirit of the invention. In another example, one of the opposed blades on the fixed support portion or the pivoting portion, or both, may be eliminated, thereby constituting a two or three bladed reamer only. In some instances, some features of the present invention may be employed only. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical reamer for cutting a bone socket, comprising:
   a) a drive shaft comprising a distal drive shaft portion extending along a drive axis to a proximal drive interface connectable to a rotary drive mechanism;
   b) at least one fixed blade member comprising a proximal fixed blade portion secured to the drive shaft and extending in at least one radial direction to a distal fixed blade portion, wherein at least one fixed cutting blade extends upwardly from the distal portion of the fixed blade member;
   c) a support shaft comprising a proximal support shaft portion secured to the proximal portion of the fixed blade member and extending to a distal support shaft portion;
   d) at least one pin secured to the fixed blade member, the pin having a pin axis spaced from, but parallel to the drive axis;
   e) at least one pivotable blade member comprising a proximal pivotable blade portion having an opening pivotably supported on the support shaft and extending in at least one radial direction to a distal pivotable blade portion, wherein at least one pivotable cutting blade extends upwardly from the distal portion of the pivotable blade member;
   f) at least one circumferential slot provided in the pivotable blade member with the fixed pin received in the slot;
   g) a biasing member biasing between the pivotable blade member and the distal portion of the support shaft to thereby maintain a selected pivoted relationship between the pivotable blade member and the fixed blade member; and
   h) wherein the pivotable blade member is selectively pivotable toward and away from the fixed blade member to either expand or contract the reamer in relative overall size, such that:
      i) when the reamer is in a fully contracted configuration, the fixed cutting blade and the pivotable cutting blade are in a closely spaced relationship with the fixed pin abutting one end of the circumferential slot in the pivotable blade member; and
      ii) when the reamer is in a fully expanded configuration, the fixed cutting blade and the pivotable cutting blade are in a spaced apart relationship with the fixed pin abutting an opposite end of the circumferential slot to thereby block further spaced apart rotational movement of the at least one fixed cutting blade relative to the at least one pivotable cutting blade when cutting bone.

2. The surgical reamer of claim 1 wherein at least one of the fixed blade member and the pivoting blade member has two cutting blades extending upwardly from the distal fixed blade portion or the distal pivotable blade portion, as the case may be, spaced apart from one another with the reamer in the fully expanded configuration.

3. The reamer of claim 1 wherein the fully contracted configuration is a position in which the pivotable blade member and the fixed blade member are collapsed into a relatively small overall size, thus facilitating insertion of the reamer through an incision.

4. The reamer of claim 1 wherein rotation of the reamer against tissue creates friction which acts to open the reamer from the fully contracted position into the fully expanded position.

5. The reamer of claim 1 wherein the fixed cutting blade and the pivotable cutting blade have discrete cutting sites with raised teeth.

6. The reamer of claim 1 wherein the fixed cutting blade and the pivotable cutting blade comprise arcuate blades.

7. The reamer of claim 1 wherein in the fully expanded configuration, the fixed cutting blade and the pivotable cutting blade define a hollow concave domed portion for positioning the reamer in the bone socket and then collecting surgical debris during reaming.

8. A surgical kit for cutting a bone socket, the surgical kit comprising a plurality of reamers having an array of sizes corresponding to the needs of individual patients, each reamer comprising:
   a) a drive shaft comprising a distal drive shaft portion extending along a drive axis to a proximal drive interface connectable to a rotary drive mechanism;
   b) at least one fixed blade member comprising a proximal fixed blade portion secured to the drive shaft and extending in at least one radial direction to a distal fixed blade portion, wherein at least one fixed cutting blade extends upwardly from the distal portion of the fixed blade member;
   c) a support shaft comprising a proximal support shaft portion secured to the proximal portion of the fixed blade support member and extending to a distal support shaft portion;
   d) at least one pin secured to the fixed blade member, the pin having a pin axis spaced from, but parallel to the drive axis;
   e) at least one pivotable blade member comprising a proximal pivotable blade portion having an opening pivotably supported on the support shaft and extending in at least one radial direction to a distal pivotable blade portion, wherein at least one pivotable cutting blade extends upwardly from the distal portion of the pivotable blade member;
   f) at least one circumferential slot provided in the pivotable blade member with the fixed pin received in the slot;
   g) a biasing member biasing between the pivotable blade member and the distal portion of the support shaft to thereby maintain a selected pivoted relationship between the pivotable blade member and the fixed blade member; and
   h) wherein the pivotable blade member is selectively pivotable toward and away from the fixed blade member to either expand or contract the reamer in relative overall size, such that:
      i) when the reamer is in a fully contracted configuration, the fixed cutting blade and the pivotable cutting blade are in a closely spaced relationship with the fixed pin abutting one end of the circumferential slot in the pivotable blade member; and
      ii) when the reamer is in a fully expanded configuration, the fixed cutting blade and the pivotable cutting blade are in a spaced apart relationship with the fixed pin abutting an opposite end of the circumferential slot to thereby block further spaced apart rotational movement of the at least one fixed cutting blade relative to the at least one pivotable cutting blade when cutting bone;
   i) a holder for grasping the drive interface of one of the reamers, the holder including a quick-disconnect coupling for engaging and disengaging the reamer with a source of rotary power; and
   j) a case for conveniently storing the reamers and the holder.

9. The reamer of claim 8 wherein the fixed cutting blade and the pivotable cutting blade have discrete cutting sites with raised teeth.

10. The reamer of claim 8 wherein the fixed cutting blade and the pivotable cutting blade comprise arcuate blades.

11. The reamer of claim 8 wherein in the fully expanded configuration, the reamer defines a hollow concave domed structure suitable for collecting surgical debris during reaming and which is then collapsible into the fully contracted position for removal of the reamer through an incision.

12. The surgical kit of claim 8 wherein rotation of the reamer against tissue creates friction which acts to open the reamer from the fully contracted position into the fully expanded position.

13. The surgical kit of claim 8 wherein a connector bar extends between the two cutting blades extending upwardly from the at least one of the fixed blade support member and the pivoting blade member.

14. A surgical reamer for cutting a bone socket, comprising:
   a) a drive shaft comprising a distal drive shaft portion extending along a drive axis to a proximal drive interface connectable to a rotary drive mechanism;
   b) at least one fixed blade member comprising a proximal fixed blade portion secured to the drive shaft and extending in at least one radial direction to a distal fixed blade portion, wherein at least one fixed cutting blade extends upwardly from the distal portion of the fixed blade member;
   c) a support shaft comprising a proximal support shaft portion secured to the proximal portion of the fixed blade member and extending to a distal support shaft portion;
   d) at least one pin secured to the fixed blade support member, the pin having a pin axis spaced from, but parallel to the drive axis;
   e) at least one pivotable blade member comprising a proximal pivotable blade portion having an opening pivotably supported on the support shaft and extending in at least one radial direction to a distal pivotable blade portion, wherein at least one pivotable cutting blade extends upwardly from the distal portion of the pivotable blade member;
   f) at least one circumferential slot provided in the pivotable blade member with the fixed pin received in the slot;
   g) a biasing member biasing between the pivotable blade member and the distal portion of the support shaft to thereby maintain a selected pivoted relationship between the pivotable blade member and the fixed blade member; and
   h) wherein the pivotable blade member is rotatable toward the fixed blade member to provide the reamer in a fully contracted configuration with the fixed cutting blade and the pivotable cutting blade being in a closely spaced relationship having the fixed pin abutting one end of the circumferential slot in the pivotable blade member; and
   i) wherein the pivotable blade member is rotatable against tissue to thereby create friction which acts to open the reamer from the fully contracted position to the fully expanded configuration with the fixed cutting blade and the pivotable cutting blade being in a spaced apart relationship having the fixed pin abutting an opposite end of the circumferential slot to thereby block further spaced apart rotational movement of the at least one fixed cutting blade relative to the at least one pivotable cutting blade when cutting bone.

15. A surgical reamer for cutting a bone socket, comprising:
   a) a drive shaft means extending along a drive axis from a distal drive shaft portion to a proximal drive interface connectable to a rotary drive mechanism;
   b) at least one fixed blade member comprising a proximal fixed blade portion secured to the drive shaft means and extending in a radial direction to a distal fixed blade portion, wherein at least one fixed cutting blade extends upwardly from the distal portion of the fixed blade member;
   c) at least one pin secured to the fixed blade member, the pin having a pin axis spaced from, but parallel to the drive axis;
   d) at least one pivotable blade member comprising a proximal pivotable blade portion having an opening pivotably supported on the drive shaft means and extending in a radial direction to a distal pivotable blade portion, wherein at least one pivotable cutting blade extends upwardly from the distal portion of the pivotable blade member;
   e) at least one circumferential slot provided in the pivotable blade member with the fixed pin received in the slot;
   f) a biasing member biasing between the pivotable blade member and the distal portion of the drive shaft means to thereby maintain a selected pivoted relationship between the pivotable blade member and the fixed blade member; and
   g) wherein the pivotable blade member is selectively pivotable toward or away from the fixed blade member to either expand and contract the reamer in relative overall size, such that:
      i) when the reamer is in a fully contracted configuration, the fixed cutting blade and the pivotable cutting blade are in a closely spaced relationship with the fixed pin abutting one end of the circumferential slot in the pivotable blade member; and
      ii) when the reamer is in a fully expanded configuration, the fixed cutting blade and the pivotable cutting blade are in a spaced apart relationship with the fixed pin abutting an opposite end of the circumferential slot to thereby block further spaced apart rotational movement of the at least one fixed cutting blade relative to the at least one pivotable cutting blade when cutting bone.

16. The surgical reamer of claim 15 wherein rotation of the reamer against tissue creates friction which acts to open the reamer from the fully contracted position into the fully expanded position.

17. A surgical reamer for cutting a bone socket, comprising:
   a) a drive shaft comprising a distal drive shaft portion extending along a drive axis to a proximal drive interface connectable to a rotary drive mechanism;
   b) a fixed blade member comprising opposed portions extending radially from a proximal fixed blade portion secured to the drive shaft to respective distal portions of the fixed blade member, wherein at least one fixed cutting blade extends upwardly from the distal portions of each of the fixed blade portions;
   c) a support shaft comprising a proximal support shaft portion secured to the proximal fixed blade portion and extending to a distal support shaft portion;
   d) at least one fixed pin secured to the fixed blade member, the pin having a pin axis spaced from, but parallel to the drive axis;
   e) a pivotable blade member comprising a proximal pivotable blade portion having an opening pivotably supported on the support shaft and extending in opposed radial directions to two distal pivotable blade portions, wherein at least one pivotable cutting blade extends upwardly from each of the distal pivotable portions;
   f) at least one circumferential slot provided in the pivotable blade member with the fixed pin received in the slot;
   g) a biasing member biasing between the pivotable blade member and the distal portion of the support shaft to thereby maintain a selected pivoted relationship between the pivotable blade member and the fixed blade member; and
   h) wherein the pivotable blade member is selectively pivotable toward and away from the fixed blade member to either expand or contract the reamer in relative overall size, such that:
      i) when the reamer is in a fully contracted configuration, the fixed cutting blades and the pivotable cutting blades are in a closely spaced relationship with the fixed pin abutting one end of the circumferential slot in the pivotable blade member; and
      ii) when the reamer is in a fully expanded configuration, the fixed cutting blades and the pivotable cutting blades are in a spaced apart relationship with the fixed pin abutting an opposite end of the circumferential slot to thereby block further spaced apart rotational movement of the fixed cutting blades relative to the pivotable cutting blades when cutting bone.

18. The surgical reamer of claim 17 wherein rotation of the reamer against tissue creates friction which acts to open the reamer from the fully contracted position into the fully expanded position.

19. A surgical method for cutting a bone socket in a patient, comprising the steps of:
   a) providing a reamer, which comprises: a drive shaft comprising a distal drive shaft portion extending along a drive axis to a proximal drive interface connectable to a rotary drive mechanism; at least one fixed blade member comprising a proximal fixed blade portion secured to the drive shaft and extending in at least one radial direction to a distal fixed blade portion, wherein at least one fixed cutting blade extends upwardly from the distal portion of the fixed blade member; a support shaft comprising a proximal support shaft portion secured to the proximal portion of the fixed blade member and extending to a distal support shaft portion; at least one pin secured to the fixed blade member, the pin having a pin axis spaced from, but parallel to the drive axis; at least one pivotable blade member comprising a proximal pivotable blade portion having an opening pivotably supported on the support shaft and extending in at least one radial direction to a distal pivotable blade portion, wherein at least one pivotable cutting blade extends upwardly from the distal portion of the pivotable blade member; at least one circumferential slot provided in the pivotable blade member with the fixed pin received in the slot; a biasing member biasing between the pivotable blade member and the distal portion of the support shaft to thereby maintain a selected pivoted relationship between the pivotable blade member and the fixed blade member;

and wherein the pivotable blade member is selectively pivotable toward and away from the fixed blade member to either expand or contract the reamer in relative overall size, such that:

i) when the reamer is in a fully contracted configuration, the fixed cutting blade and the pivotable cutting blade are in a closely spaced relationship with the fixed pin abutting one end of the circumferential slot in the pivotable blade member; and ii) when the reamer is in a fully expanded configuration, the fixed cutting blade and the pivotable cutting blade are in a spaced apart relationship with the fixed pin abutting an opposite end of the circumferential slot to thereby block further spaced apart rotational movement of the at least one fixed cutting blade relative to the at least one pivotable cutting blade when cutting bone;

b) providing a holder coupled to a source of rotary power;

c) releasably connecting the drive interface of the reamer to the holder;

d) collapsing the reamer into the fully contracted configuration having a less invasive insertion profile and passing the reamer through a surgical incision thence to the bone socket in the appropriate position for cutting;

e) powering the reamer in the bone socket to expand the reamer into the fully expanded configuration and then reaming the bone socket as required;

f) turning the reamer in a direction opposite to the cutting direction, thus causing the pivotable blade member and the fixed blade member to move into the fully contracted configuration having a smaller, less invasive insertion profile; and g) removing the reamer, with its collected debris, back through the incision.

20. The method of claim 19 including providing the fixed cutting blade and the pivotable cutting blade having discrete cutting sites with raised teeth.

21. The method of claim 19 including providing the fixed cutting blade and the pivotable cutting blade being arcuate blades.

22. The method of claim 19 including when the reamer is in the fully expanded configuration, the reamer defines a hollow concave domed structure suitable for collecting surgical debris during reaming and then collapsing the reamer into the fully contracted position for removal through an incision.

* * * * *

UNITED STATES PATENT AND TRADEMARK OFFICE
CERTIFICATE OF CORRECTION

PATENT NO. : 7,608,076 B2
APPLICATION NO. : 11/380006
DATED : October 27, 2009
INVENTOR(S) : Mahmoud Ezzedine It is certified that error appears in the above-identified patent and that said Letters Patent is hereby corrected as shown below:

Title page (*) Notice: "This patent is subject to a terminal disclaimer." should be deleted.

Signed and Sealed this

Seventeenth Day of August, 2010

David J. Kappos
*Director of the United States Patent and Trademark Office*